US008641699B2

(12) United States Patent
Hansen

(10) Patent No.: US 8,641,699 B2
(45) Date of Patent: Feb. 4, 2014

(54) SYSTEMS AND METHODS FOR HERNIA REPAIR

(76) Inventor: Adam J. Hansen, Tucson, AZ (US)

(*) Notice: Subject to any disclaimer, the term of this patent is extended or adjusted under 35 U.S.C. 154(b) by 1225 days.

(21) Appl. No.: 12/418,579

(22) Filed: Apr. 4, 2009

(65) Prior Publication Data

US 2010/0256611 A1 Oct. 7, 2010

(51) Int. Cl.
*A61B 17/00* (2006.01)
(52) U.S. Cl.
USPC .................................. 606/1; 604/48
(58) Field of Classification Search
USPC .......... 606/1, 108, 127, 151, 213; 604/48, 59, 604/61
See application file for complete search history.

(56) References Cited

U.S. PATENT DOCUMENTS

| | | | |
|---|---|---|---|
| 5,147,374 A | 9/1992 | Fernandez | |
| 5,304,187 A | 4/1994 | Green et al. | |
| D347,061 S | 5/1994 | Phillips | |
| 5,366,460 A | 11/1994 | Eberbach | |
| 5,397,332 A | 3/1995 | Kammerer | |
| 5,405,360 A | 4/1995 | Tovey | |
| 5,464,403 A | 11/1995 | Kieturakis | |
| 5,540,704 A * | 7/1996 | Gordon et al. | 606/144 |
| 5,618,290 A | 4/1997 | Toy et al. | |
| 5,865,802 A | 2/1999 | Yoon et al. | |
| 6,409,739 B1 * | 6/2002 | Nobles et al. | 606/148 |
| 6,575,988 B2 | 6/2003 | Rousseau | |
| 7,727,142 B2 * | 6/2010 | Hjelle et al. | 600/37 |
| 2007/0112361 A1 | 5/2007 | Schonholz et al. | |
| 2007/0260179 A1 | 11/2007 | Sholev et al. | |
| 2008/0188874 A1 | 8/2008 | Henderson | |

* cited by examiner

*Primary Examiner* — Victor Nguyen
(74) *Attorney, Agent, or Firm* — Baker & Associates PLLC; Trent Baker

(57) ABSTRACT

One embodiment of the present invention relates to a minimally invasive implant-based ventral hernia repair system including a first and second elongated member in which the second elongated member extends through the internal channel of the first elongated member. A set of arm members are moveably coupled to the distal end of the first elongated member. A set of tension members extends lengthwise along the arm members and is rigidly coupled between the distal most segment of each arm member and the second elongated member. The degree of tension in the tension members corresponds to the configuration of the arm members with respect to the first elongated member. The proximal translation of the second elongated with respect to the first elongated member causes tension on the tension members, which thereby articulates the arm members into a radial extended configuration in which the arm members extend radially and substantially perpendicular to the first elongated member.

22 Claims, 9 Drawing Sheets

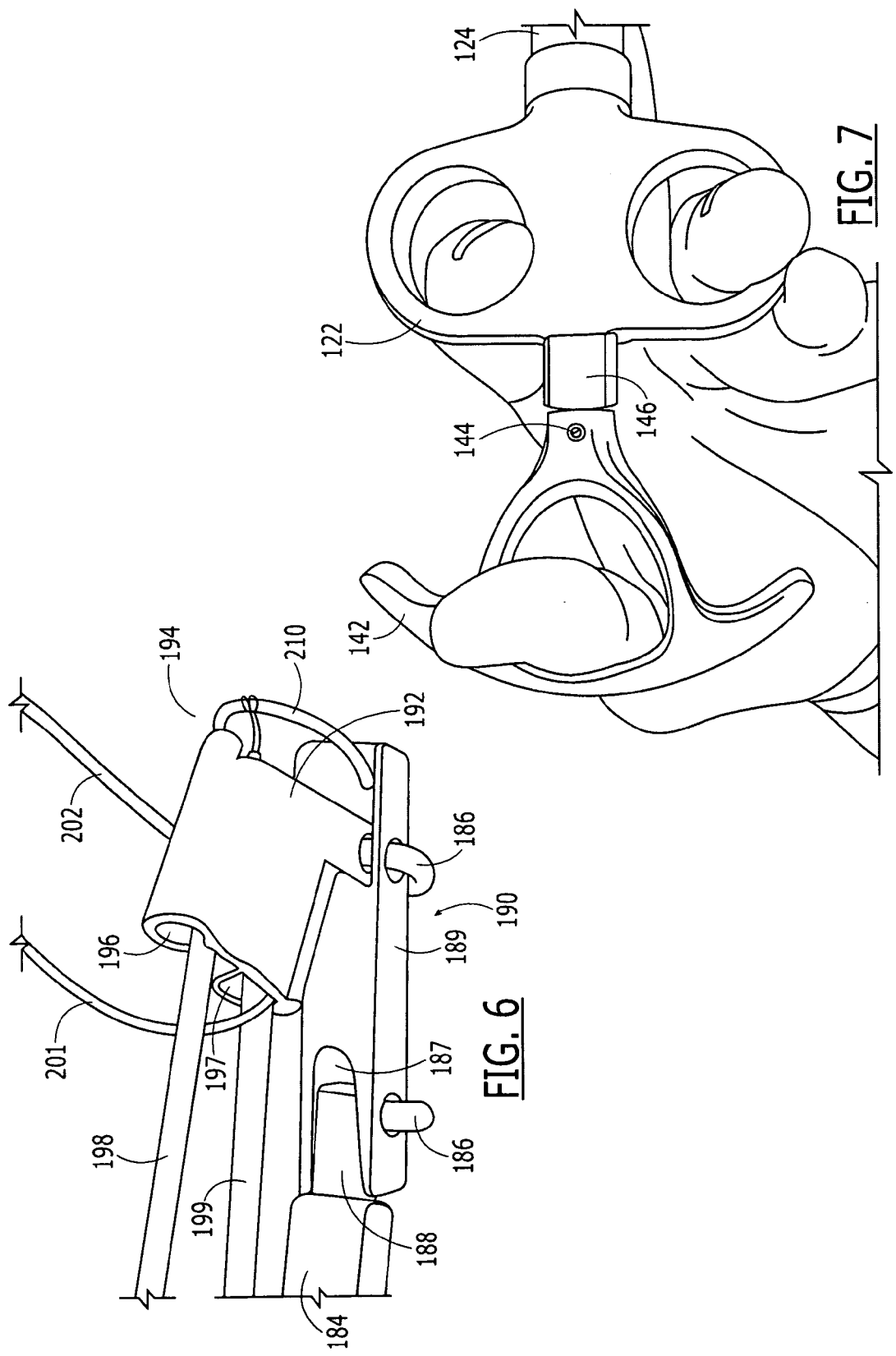

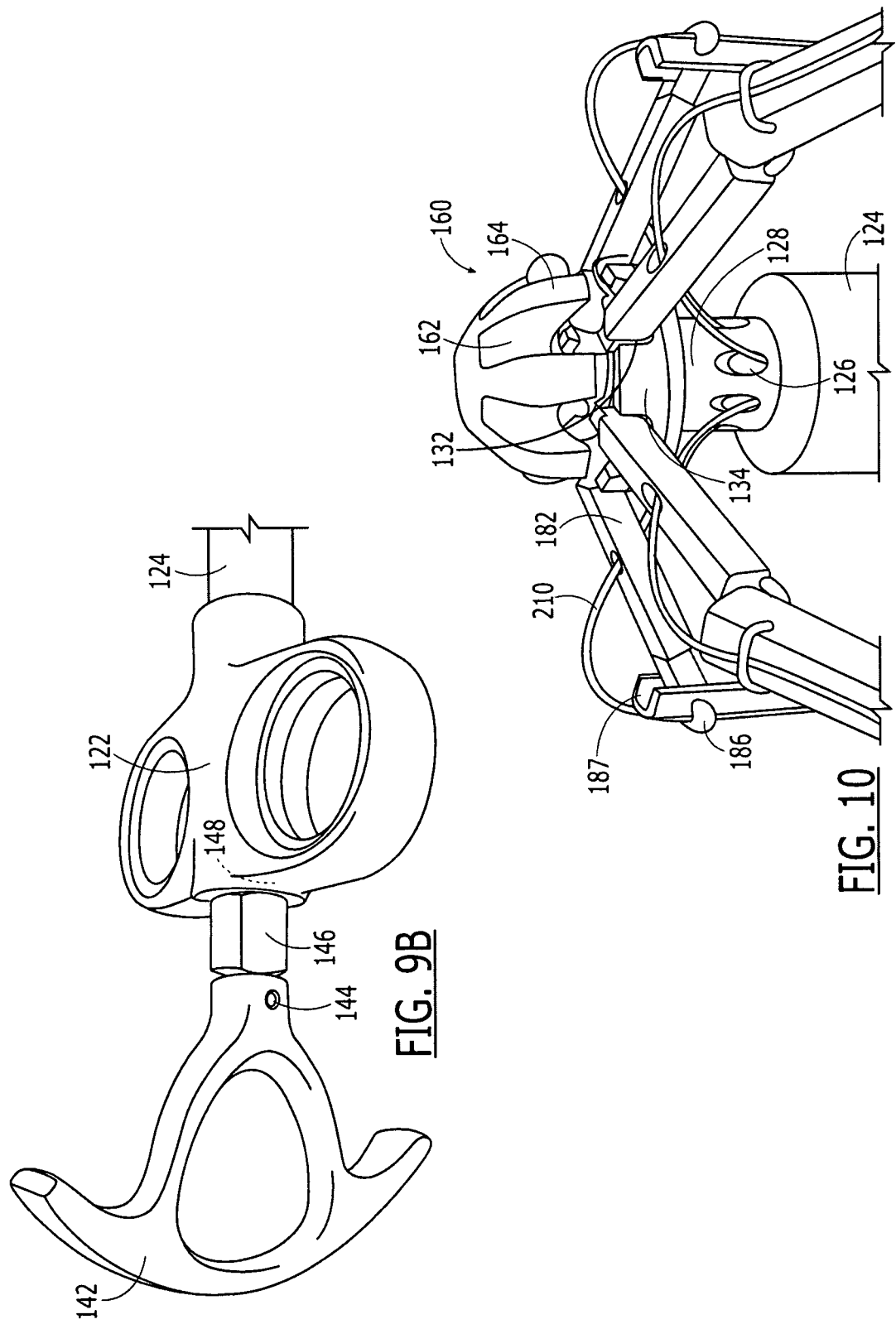

SYSTEMS AND METHODS FOR HERNIA REPAIR

FIELD OF THE INVENTION

The invention generally relates to minimally invasive hernia repair systems. In particular, the present invention relates to a minimally invasive implant-based ventral hernia repair system and method of operation.

BACKGROUND OF THE INVENTION

A hernia is a weakness in a particular anatomical surface which allows an internally contained organ to protrude. Ventral hernias are a type of hernia resulting primarily from weaknesses in the abdominal wall. Hernias of the groin region, or inguinal hernias, are a separate type of abdominal wall hernia which are repaired with a different subset of surgical equipment and techniques. Repair of ventral hernia defects conventionally utilized open primary sutured repair. However, recurrence rates of ventral hernias after an open primary suture procedure were determined to be unacceptably high. Open mesh repair utilizes a synthetic or biologic mesh to correct the hernia but is still performed as an open invasive procedure. Open mesh repair has recently been replaced by laparoscopic, or minimally invasive, mesh repair. Recurrence rates have been shown to be lower after laparoscopic ventral hernia repair with respect to open repair. Laparoscopic type hernia repair reduces dissection and destruction of the structurally important fascial layers of the abdominal wall via the use of small incisions in the fascia, through which trocars are placed for instrumentation. Unfortunately, even small (i.e. 5 mm) incisions can potentially develop into new hernias, especially in patients with a demonstrated propensity to developing fascial breakdown. Therefore, fewer trocars utilized to perform an operation generally results in a lower recurrence rate. Conventional laparoscopic surgical techniques for ventral hernia repair commonly require up to six trocars and corresponding incisions for proper manipulation of instruments and mesh implants.

Therefore, there is a need in the industry for systems and methods that reduce the number of trocars necessary for minimally invasive implant-based ventral hernia repair.

SUMMARY OF THE INVENTION

The invention generally relates to minimally invasive hernia repair systems. One embodiment of the present invention relates to a minimally invasive implant-based ventral hernia repair system. The system includes a first elongated member with an internal channel extending between a distal and proximal opening. A second elongated member extends through the internal channel of the first elongated member. A set of arm members is moveably coupled to the distal end of the first elongated member such that the arm members have a restricted freedom of movement with respect to the first elongated member. The arm members each include a set of lengthwise moveably intercoupled segments. A set of tension members extends lengthwise along the arm members and is rigidly coupled between the distal most segment of each arm member and the second elongated member. The degree of tension in the tension members corresponds to the configuration of the arm members with respect to the first elongated member. The proximal translation of the second elongated with respect to the first elongated member causes tension on the tension members, which thereby articulates the arm members into a radial extended configuration in which the arm members extend radially and substantially perpendicular to the first elongated member. A mesh is releasably coupled to the distal side of the arm members to facilitate coupling over the corresponding hernia. The moveable couplings between the arm members and the first elongated member and between the intercoupled segments of the arm members facilitates a restricted lengthwise freedom of movement that enables the system to be coupled to the mesh over the hernia and to be removable from between the mesh and hernia. A second embodiment of the present invention relates to a method of distally coupling a mesh over a ventral hernia in the abdominal wall and subsequently removing the remainder of the hernia repair system.

Embodiments of the present invention represent a significant advancement in the field of ventral hernia repair. Conventional minimally invasive ventral hernia repair systems and procedures utilize multiple instruments and openings in the abdominal wall to position and suture a mesh or implant over the hernia. Embodiments of the present invention provide a self-contained system for hernia mesh deployment and suturing through the hernia opening itself. The unique selectively restricted movement freedom of the arm members enables the system to be inserted through the internal channel of a trocar, coupled with a mesh over the distal opening of a hernia, and the remainder removed from between the mesh and hernia. This presents an advantage because the number of abdominal wall openings made in a hernia repair procedure has been determined to directly correspond to hernia recurrence rate.

These and other features and advantages of the present invention will be set forth or will become more fully apparent in the description that follows and in the appended claims. The features and advantages may be realized and obtained by means of the instruments and combinations particularly pointed out in the appended claims. Furthermore, the features and advantages of the invention may be learned by the practice of the invention or will be obvious from the description, as set forth hereinafter.

BRIEF DESCRIPTION OF THE DRAWINGS

The following description of the invention can be understood in light of the Figures, which illustrate specific aspects of the invention and are a part of the specification. Together with the following description, the Figures demonstrate and explain the principles of the invention. In the Figures, the physical dimensions may be exaggerated for clarity. The same reference numerals in different drawings represent the same element, and thus their descriptions will be omitted.

FIG. 6 illustrates a detailed perspective view of the distal segment of a single arm member of the hernia repair system illustrated in FIG. 1;

FIG. 7 illustrates a profile view of the proximal ends of the first and second elongated member of the hernia repair system illustrated in FIG. 1;

FIGS. 9A-9B illustrate perspective views of the proximal ends of the first and second elongated member corresponding to two different operational states of the hernia repair system illustrated in FIG. 1;

FIG. 10 illustrates a detailed perspective view of the distal ends of the first and second elongated members in an unlocked configuration of the hernia repair system illustrated in FIG. 1;

DETAILED DESCRIPTION OF THE INVENTION

Figure 1:
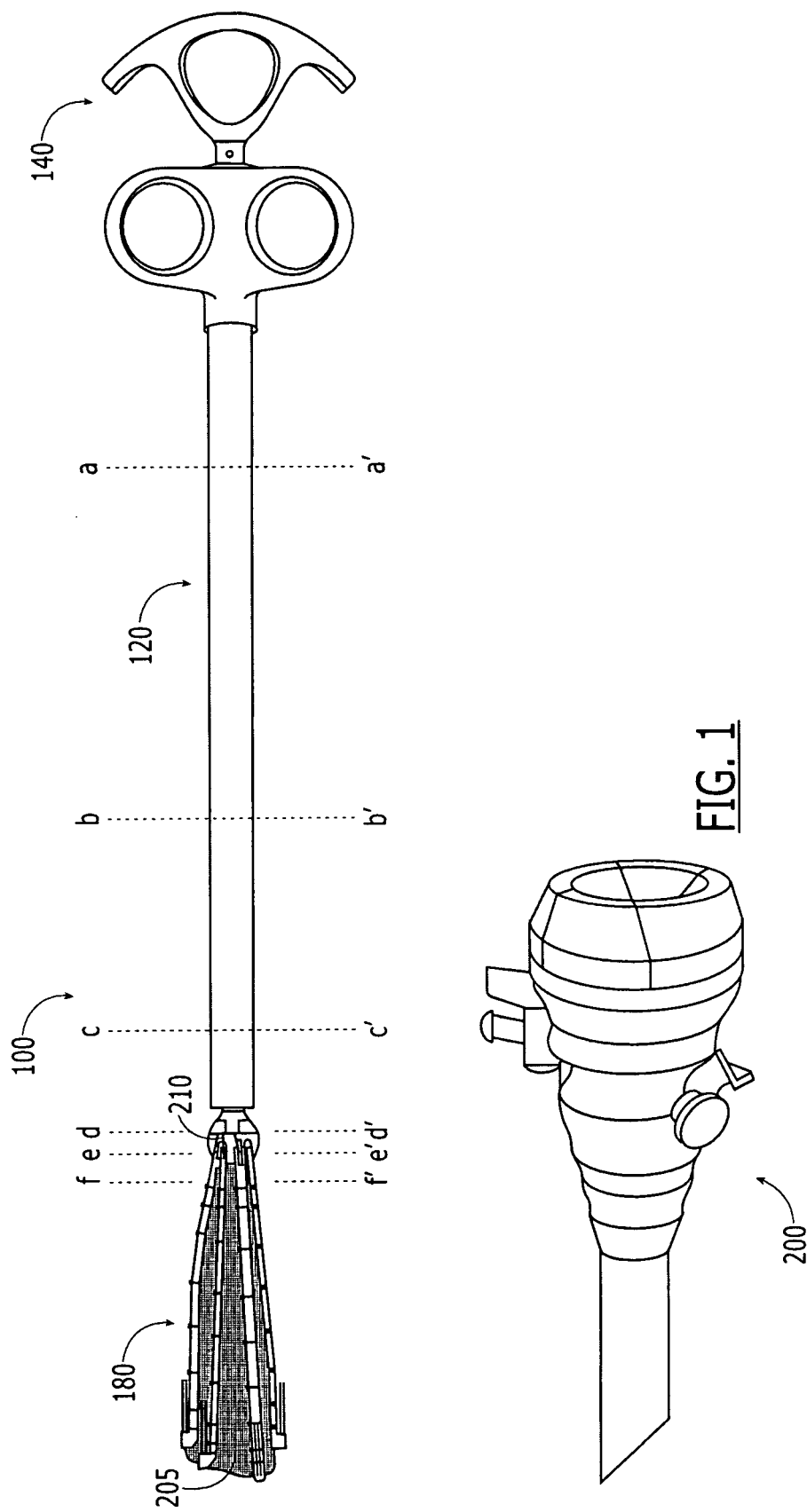
FIG. 1 illustrates a perspective view of a hernia repair system and corresponding trocar in accordance with one embodiment of the present invention.

The invention generally relates to minimally invasive hernia repair systems. One embodiment of the present invention relates to a minimally invasive implant-based ventral hernia repair system. The system includes a first elongated member with an internal channel extending between a distal and proximal opening. A second elongated member extends through the internal channel of the first elongated member. A set of arm members is moveably coupled to the distal end of the first elongated member such that the arm members have a restricted freedom of movement with respect to the first elongated member. The arm members each include a set of lengthwise moveably intercoupled segments. A set of tension members extends lengthwise along the arm members and is rigidly coupled between the distal most segment of each arm member and the second elongated member. The degree of tension in the tension members corresponds to the configuration of the arm members with respect to the first elongated member. The proximal translation of the second elongated with respect to the first elongated member causes tension on the tension members, which thereby articulates the arm members into a radial extended configuration in which the arm members extend radially and substantially perpendicular to the first elongated member. A mesh is releasably coupled to the distal side of the arm members to facilitate coupling over the corresponding hernia. The moveable couplings between the arm members and the first elongated member and between the intercoupled segments of the arm members facilitates a restricted lengthwise freedom of movement that enables the system to be coupled to the mesh over the hernia and to be removable from between the mesh and hernia. A second embodiment of the present invention relates to a method of distally coupling a mesh over a ventral hernia in the abdominal wall and subsequently removing the remainder of the hernia repair system. Also, while embodiments are described in reference to ventral hernia repair, it will be appreciated that the teachings of the present invention are applicable to other areas. For example, embodiments and teachings of the present invention may be utilized to repair other types of hernias.

The following terms are defined as follows:

Endoscopic surgery—broadly defined to include all minimally invasive surgical procedures, including but not limited to laparoscopy, thoracoscopy and arthroscopy.

Hernia—a weakness or recess in a particular anatomical surface which allows an internally contained organ to protrude. The internal side of the herniated surface is referred to herein as the distal side. The external side of the herniated surface is referred to herein as the proximal side. A particular type of hernia referred to as a ventral hernia involves a weakness in the abdominal wall.

Trocar—a cylindrical device which may be inserted through a surgical incision to provide a channel through a body wall to the intended internal surgical region.

Distal—an anatomical surgical reference term used herein to refer to a region toward the body of the patient. For example, a trocar disposed within a patient is oriented such that the distal end is disposed within the surgical field and/or the patient's body.

Proximal—an anatomical surgical reference term used herein to refer to a region away from the body of the patient. For example, a trocar disposed within a patient is oriented such that the proximal end is disposed external to the patient's body.

Mesh—a general term used to describe any synthetic or biologic implant configured to extend over and cover the internal opening/weakness of a hernia.

Needle—a general term used to describe any suture device configured to couple a mesh over a hernia.

Reference is initially made to FIG. 1, which illustrates a perspective view of a hernia repair system and corresponding trocar, designated respectively at 100 and 200. Minimally invasive hernia repair procedures initially include inserting a trocar through the herniated surface, thereby creating a proximal to distal channel through the hernia in the abdominal wall. The trocar provides an access channel through which instruments may be inserted distal to the hernia. Conventional laparoscopic hernia repair procedures require the insertion of additional trocars in the vicinity of the hernia to enable additional instruments to access the distal side of the herniated surface. Embodiments of the present invention include a system that is designed to operate exclusively through a single trocar 200 positioned through the hernia. The illustrated hernia repair system 100 is configured to be inserted through the internal channel of the trocar 200 onto the distal side of the hernia so as to expand and implant a repair mesh over the hernia. The illustrated trocar 200 is for reference purposes only, and it will be appreciated that the illustrated embodiment may be utilized with other trocars.

The hernia repair system 100 includes a first elongated member 120, a second elongated member 140, a plurality of tension members 210, and a plurality of arm members 180. The illustrated first elongated member 120 is cylindrically shaped with a particular external diameter and curvature corresponding to the diameter of the internal channel of the illustrated trocar 200. It will be appreciated that various diameters and shapes may be utilized in accordance with embodiments of the present invention. In addition, the external surface of the first elongated member 120 is configured to facilitate a smooth translation within the internal channel of the trocar 200. The first elongated member 120 is illustrated with a distal end oriented towards the left and a proximal end oriented to the right. The plurality of arm members 180 are moveably coupled to the distal end of the first elongated member 120. The plurality of arm members 180 are distally extended and capable of three dimensionally conforming to the diameter of the internal channel of the trocar 200. The second elongated member 140 is lengthwise extended through the first elongated member 120. The second elongated member 140 is illustrated with a distal end towards the left and a proximal end oriented to the right. The operation, assembly, and technical specifications of each of the components of the hernia repair system 100 will be described further in reference to the subsequent figures.

Figure 2:
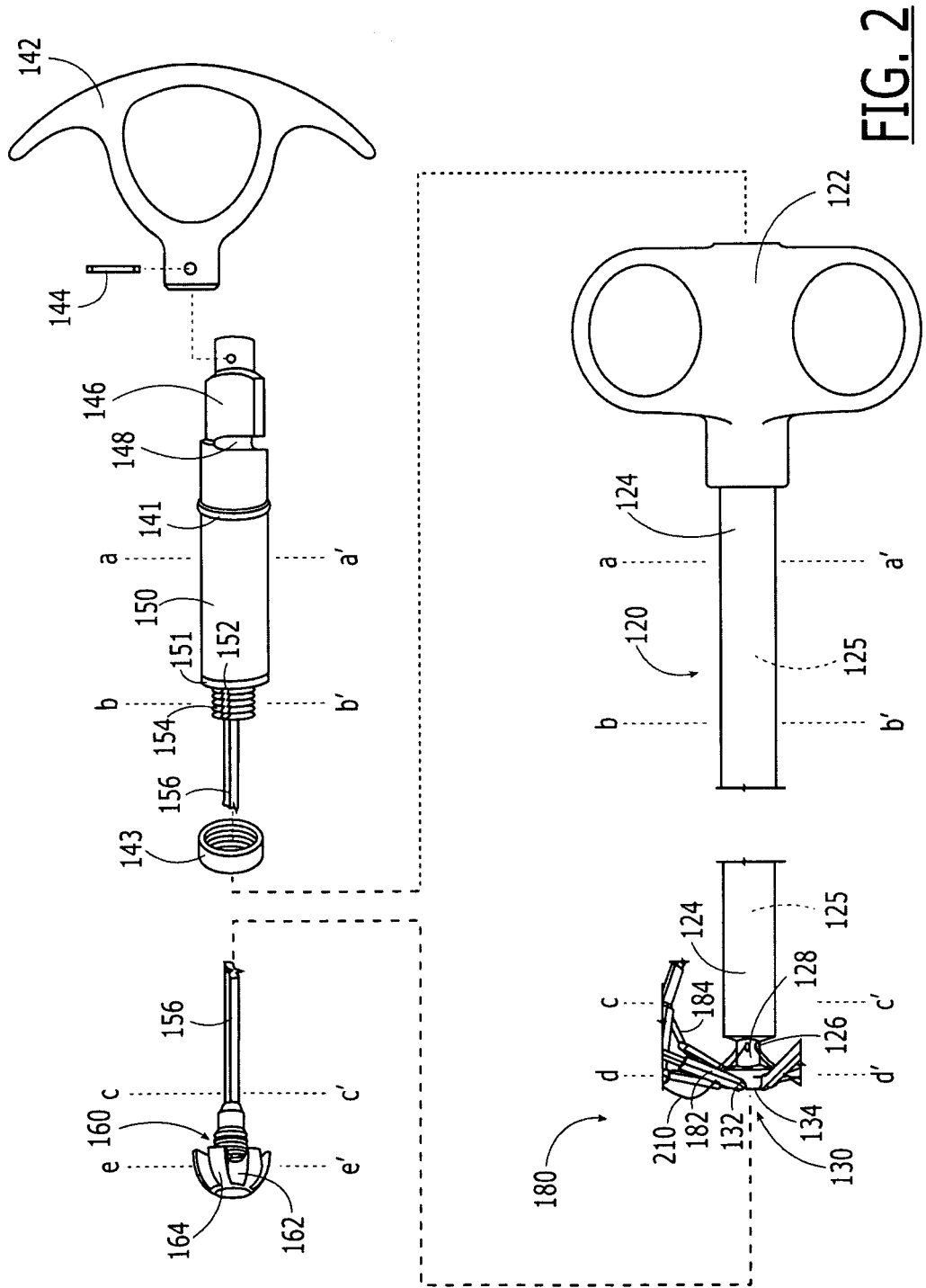
FIG. 2 illustrates an exploded view of the hernia repair system illustrated in FIG. 1.

Reference is next made to FIG. 2, which illustrates an exploded view of the hernia repair system 100. The hernia repair system 100 generally includes a first elongated member 120, a second elongated member 140, a plurality of arm members 180, and a plurality of tension members 210. The first elongated member 120 includes a cylindrical region 124, a proximal end 122, an internal channel 125, and a distal end 130. The cylindrical region 124 is an elongated hollow member which may be composed of a rigid metal material such as stainless steel or aluminum. The cylindrical region 124 is positioned between the proximal and distal ends 122, 130 of the first elongated member 120. The internal channel 125 extends lengthwise within the cylindrical region 124. The particular external shape, diameter, and surface texture of the cylindrical region 124 are configured to correspond to the diameter of the internal channel of a trocar. The proximal end 122 includes a dual recess handle shaped region to facilitate operation. It will be appreciated that various handle shapes may be utilized to accommodate different functionalities. The illustrated dual recess shape provides a surface upon which a user's fingers may oppose a distal or proximal oriented thumb force upon the second elongated member 140 with respect to the first elongated member 120. The illustrated handle shaped region is coupled to the cylindrical region via a recess within which the cylindrical region 124 is extended. The handle region may be composed of a rigid plastic composite material. The internal channel 125 extends through the proximal end 122 and handle shaped region to a proximal opening on a proximally oriented surface of the proximal end 122. The distal end 130 includes a coupler region 128 moveably coupled to the plurality of arm members 180. The coupler region 128 includes a plurality of radially oriented recesses 126, a plurality of radially oriented arm member articulation regions 132, and a plurality of radially oriented spacer regions 134. The internal channel 125 extends through the distal end 130 to a distal opening on a distal oriented surface. The plurality of arm members 180 are moveably coupled to the distal end 130 so as to facilitate a restricted freedom of movement radially oriented within the arm member articulation regions 132. The spacer regions 134 radially space the articulation of the arm members 180 from one another. The illustrated shape of the distal end is substantially cylindrical to maintain total system conformity to within the diameter of the internal trocar channel in a particular distal extended configuration. A smaller diameter region is positioned between the cylindrical region 124 and the arm member articulation region 132. The smaller diameter region provides a transition region for the tension members 210 to extend between the internal channel 125 and the arm members 180 without radially extending beyond the diameter corresponding to the internal channel of a trocar 200. The recesses 126 are disposed in the smaller diameter region and extend between the exterior and the internal channel 125.

Figure 12:
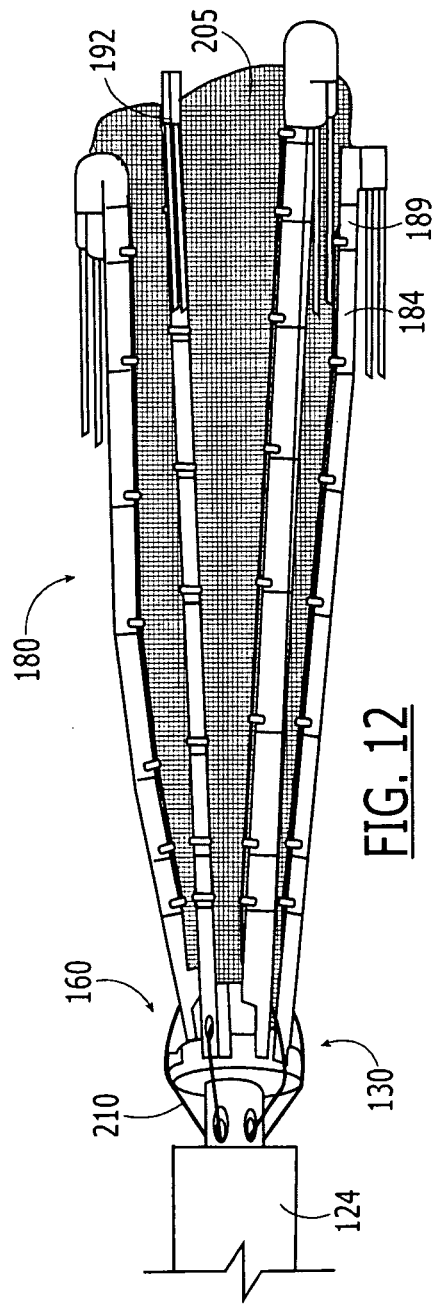
FIG. 12 illustrates a detailed perspective view of the arm members, mesh, and the distal ends of the first and second elongated members in a distal lengthwise extended, or undeployed configuration of the arm members of the hernia repair system illustrated in FIG. 1.
Figure 13:
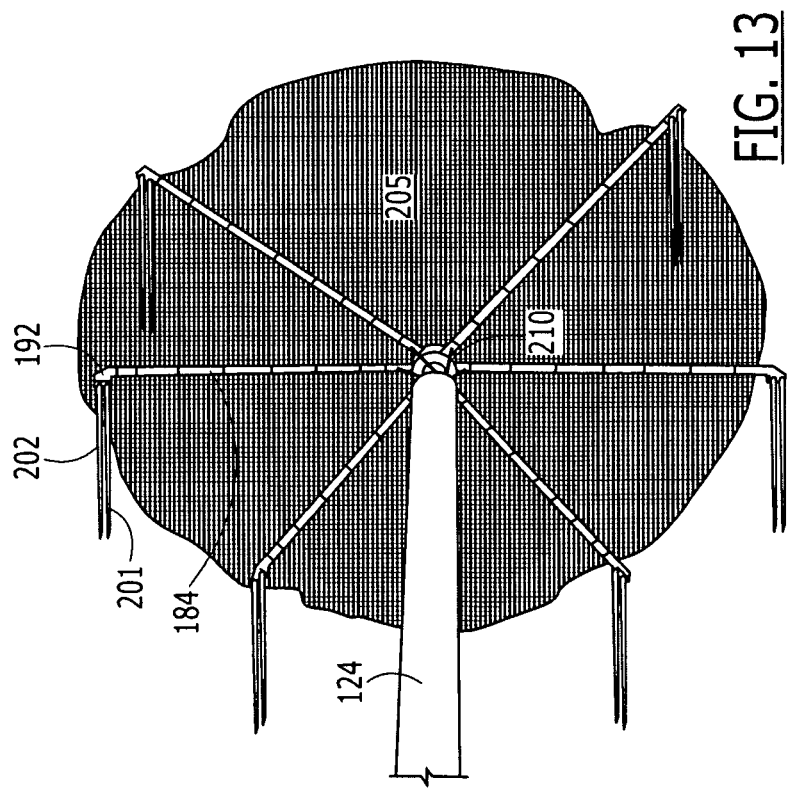
FIG. 13 illustrates a detailed perspective view of the arm members, mesh, and the distal ends of the first and second elongated members in a radial extended configuration of the arm members of the hernia repair system illustrated in FIG. 1.

The arm members 180 are moveably coupled to the distal end 130 of the first elongated member 120 to limit the articulation of the arm members 180 between a lengthwise extended distal configuration (FIG. 12) and a radial extended configuration (FIG. 13). The particular coupling between the distal end 130 and the arm members 180 may utilize a pin type connection oriented across and through the arm member articulation regions 132 and the arm members 180 so as to facilitate a substantially lengthwise (proximal to distal) oriented articulation. The shape and positioning of the pin with respect to the arm members 180 and the arm member articulation regions 132 will restrict the lengthwise freedom of articulation of the arm members 180 to within 180 degrees. The arm members 180 further include a plurality of intercoupled segments including a proximal segment 182, medial segments 184, and a distal segment 190. Configuration and specifications of the segments will be described in more detail with reference to subsequent figures. The intercoupled segments are moveably coupled to one another in a configuration that restricts relative lengthwise articulation to within 90 degrees between individual segments. The intercoupled segments may utilize a male region 188, female region 187, and a pin 186 extending perpendicular as illustrated and described further in reference to FIG. 6. The restricted moveable couplings between the distal end 130 and the proximal segment 182, and between the individual segments 182, 184, 190 operate to restrict the overall articulation freedom of the arm members 180 to between the lengthwise extended distal configuration (FIG. 12) and the radial extended configuration (FIG. 12). Various types of analogous restricted moveable coupling schemes may be utilized in accordance with embodiments of the present invention.

A plurality of tension members 210 are rigidly coupled to and extending between the distal segment 190 of each of the arm members 180 and the second elongated member 140. The tension members 210 may be any type of lengthwise substantially flexible member including but not limited to cables, sutures, threads, wires, etc. The tension members extend substantially lengthwise along the segments of the arm members 180, through the recesses 126 in the distal end 130 of the first elongated member 120 to the internal channel of the first elongated member, and are coupled to the second elongated member 140. The length and relative tension of the tension members 210 corresponds to the configuration of the plurality of arm members 180 with respect to the first elongated member 120. The tension members 210 extend substantially along the distal oriented side of the segments of the arm members 180 if the arm members 180 are positioned in the radially extended configuration (FIG. 12). The tension members 210 extend from the recesses 126 through a hole on a proximally oriented side of the proximal segment 182 in the smaller diameter region of the distal end 130 of the first elongated member 120. The coupling and length of the tension members 210 with respect to the second elongated member 140 are configured such that there is no tension if the proximal end 144 of the second elongated member is adjacent to the proximal end 122 of the first elongated member 120 (FIG. 7).

With continued reference to FIG. 2, the second elongated member 140 includes a proximal end 142, a locking pin 144, a flat region 146, a notch 148, an O-ring 141, a medial region 150, a washer 151, a threaded region 152, a nut 143, a shaft 156, and a distal end 160. As described above, the majority of the second elongated member 140 is disposed within the internal channel 125 of the first elongated member 120 during operation, with the exception of the proximal and distal ends 142, 160. The proximal end 142 includes a single recess curved handle shaped region. It will be appreciated that various handle shapes may be utilized to accommodate different functionalities. The illustrated single recess shape provides a surface upon which a user's thumb may exert a distal or proximal oriented thumb force upon the second elongated member 140 with respect to the first elongated member 120. The operational movement between the proximal ends 122, 142 of the first and second elongated members 120, 140 is in part analogous to the operation of a syringe. The proximal end 142 is operationally coupled over a corresponding cylindrical portion of the medial region 150 via the pin 144. The flat region 146 and notch 148 are shaped to facilitate an operational locking of the second elongated member 140 in a particular proximally translated and rotated position with respect to the first elongated member 120 (FIG. 9B). The shape of the flat region 146 and notch 140 correspond to the shape of the proximal opening to the internal channel 125 on the proximal end 122 of the first elongated member 120. The O-ring 141 is a rubber circular member circumscribing the medial region 150 to facilitate a smooth operational translation between the first and second elongated members 120, 140. The medial region 150 is a partially cylindrical region externally shaped to correspond to the internal channel 125 of the first elongated member 120. The rubber washer 151 and nut 143 provide a compression type coupling scheme between the tension members 210 and the second elongated member 140. In an assembled configuration (not shown), the tension members 210 extend along grooves 154 in the threaded region 152 and are compression coupled to the medial region via the rubber washer 151 and the nut 143. It will be appreciated that other types of coupling systems may be utilized between the tension members 210 and the second elongated member 140. The shaft 156 includes a non-circular cross-sectional shape so as to facilitate rotational binding with the remainder of the second elongated member 140. The illustrated shaft 156 is square shaped and disposed within a corresponding square recess within the threaded region 152 so as to enable rotational coordination between the proximal end 142 and the distal end 160 of the second elongated member 140. The proximal end of the shaft 156 is releasably disposed and/or coupled within the square recess of the threaded region 152. This configuration enables lengthwise translational separation between the shaft 156 and the threaded region 152 as the second elongated member 140 is proximally translated with respect to the first elongated member 120. The distal end 160 is directly coupled to the shaft 156 via a welding or adhesive type coupling. The distal end 160 may also be referred to as a locking member in that it functions to selectively lock the articulation freedom of the proximal segment 182 of the arm members 180. The distal end 160 of the second elongated member 140 includes the illustrated threaded male region that couples within a corresponding female threaded region on the distal end 130 of the first elongated member 120. The corresponding coupling between the threaded regions obstructs translational freedom but enables rotational freedom between the distal ends 130, 160 of the first and second elongated members 120, 140. The distal end 160 includes a plurality of radial channels 162 and radial stops 164. In an operational configuration, the shaft 156 is sized and routed through the internal channel 125 of the first elongated member 120 such that the distal end 160 is exposed and positioned further distal of the distal end 130 of the first elongated member 120 as illustrated in FIG. 3.

Figure 3:
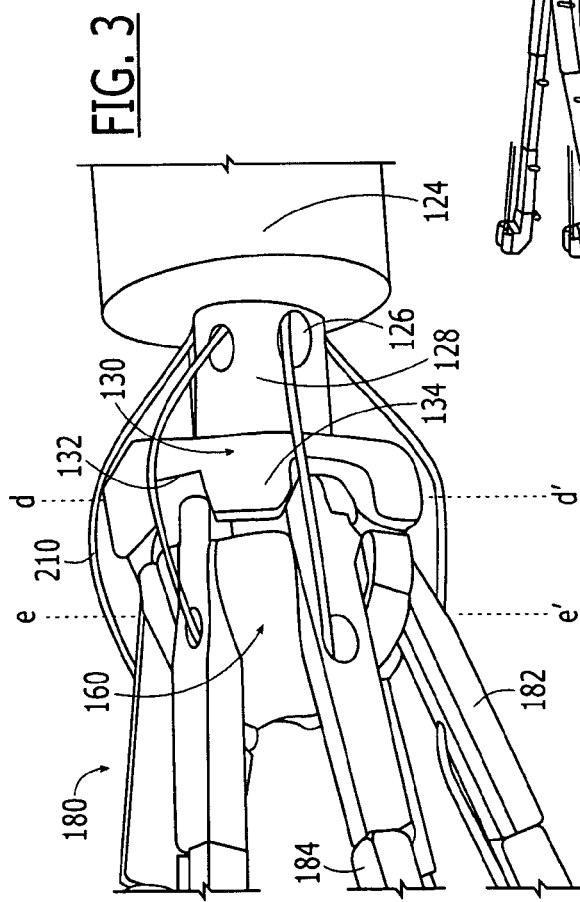
FIG. 3 illustrates a detailed perspective view of the distal end of the first and second elongated members of the hernia repair system illustrated in FIG. 1.

Reference is next made to FIG. 3, which illustrates a detailed assembled perspective view of the distal ends 130, 160 of the first and second elongated members 120, 140, the arm members 180, and the tension members 210 of the hernia repair system 100. The distal end 160 of the second elongated member 140 is distally positioned to geometrically cap the distal end 130 of the first elongated member 120. The geometric capping configuration includes aligning the radial curvatures and diameters of the distal ends 130, 160. In addition, the radial relative position of the distal ends 130, 160 with respect to one another corresponds to the articulation freedom of the arm members 180. In the illustrated configuration, the arm members 180 are distally extended from the arm articulation regions 132 of the first elongated member 120 through the radial channels 162 of the second elongated member 140. Therefore, the radial channels 162 of the second elongated member 140 are rotationally aligned with the arm articulation regions 132 of the first elongated members 120, thereby allowing the arm members 180 to articulate distally. As will be discussed in more detail below, the operation of the system 100 includes the ability for a user to rotate the second elongated member 140 with respect to the first elongated member 120, thereby rotating the radial orientations of the distal ends 130, 160 with respect to one another. The illustrated rotational orientation of the distal ends 130, 160 with respect to one another may be referred to as an unrestricted configuration because of the rotational alignment between the radial channels 162 and arm articulation region 132.

Figure 4:
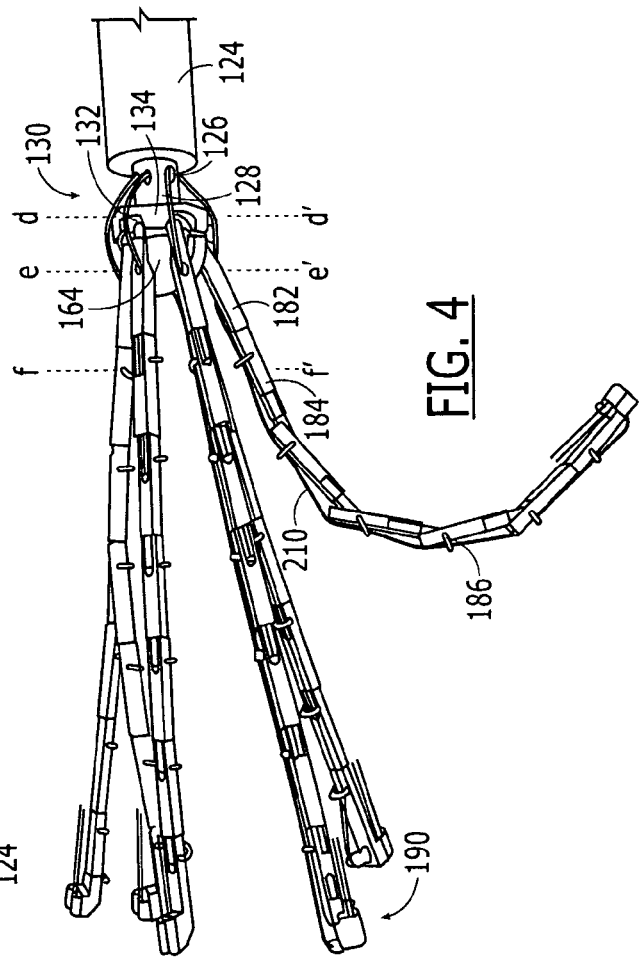
FIG. 4 illustrates a detailed perspective view of the arm members and the distal ends of the first and second elongated members of the hernia repair system illustrated in FIG. 1.

Reference is next made to FIG. 4, which illustrates a detailed assembled perspective view of the distal ends 130, 160 of the first and second elongated members 120, 140, the arm members 180, and the tension members 210 of the hernia repair system 100. FIG. 4 particularly illustrates the complete length of the arm members 180 including the proximal segment 182, medial segments 184, and distal segment 190. One of the arm members 180 is proximally lengthwise articulated including a combined articulation of individual segments 182, 184, 190, and an articulation with respect to the distal end 130 of the first elongated member 120. The illustrated segments 182, 184, 190 are intercoupled utilizing a male to female portion intercoupled with a pin 186. The particular moveable coupling scheme between the segments 182, 184, 190 will be further described with reference to FIG. 6. The tension members 210 extend lengthwise along the proximal and medial segments 182, 182 to the distal segment 190. The lengthwise side of the segments 182, 184, 190 along which the tension members 210 extend may be described as either the inward side or distal side due to the moveable positioning of the arm members 180.

Figure 5C:
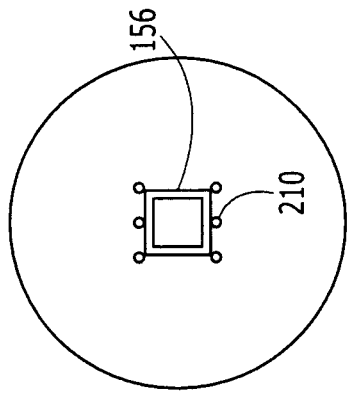
FIGS. 5A-5F illustrate cross-sectional views of the hernia repair system of FIG. 1 along the corresponding axis A-A' through F-F'.
Figure 5F:
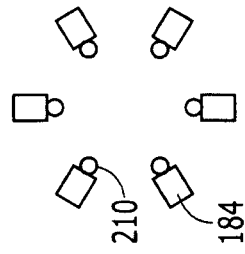
Figure 5B:
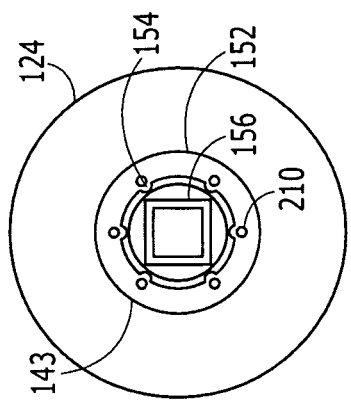
Figure 5E:
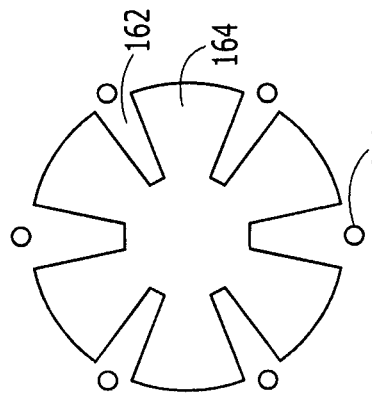
Figure 5A:
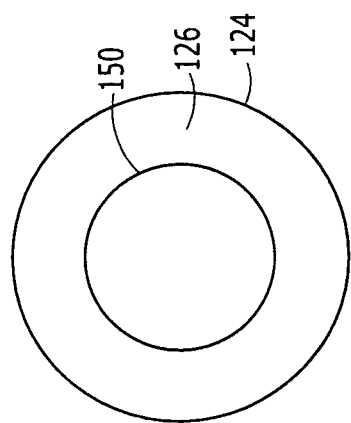
Figure 5D:
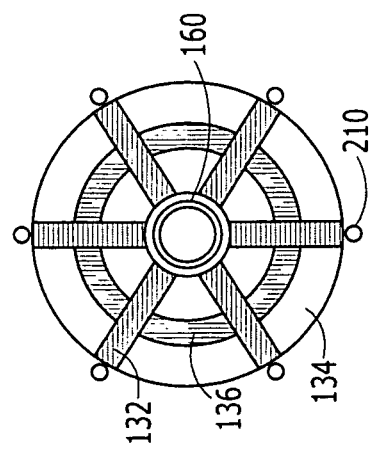

Reference is next made to FIGS. 5A-5F, which illustrate cross-sectional views of the hernia repair system of FIG. 1 along the corresponding axis designations A-A' through F-F'. FIG. 5A illustrates the medial region 150 of the second elongated member 140 disposed within the cylindrical region 125 of the first elongated member 120. The medial region 150 is specifically sized and shaped to facilitate translation within the internal channel 126 of the first elongated member 120. FIG. 5B illustrates the shaft 156 positioned within the threaded region 152 of the second elongated member 140 and the cylindrical region 150 of the first elongated member 120. In addition, the tension members 210 are routed through the grooves 154 of the threaded region 152. The tension members 210 are circumscribed and compression coupled to the threaded region 152 by the nut 143. The nut 143 is correspondingly internally threaded to couple over the threaded region 152. FIG. 5C illustrates the tension members 210 lengthwise extending along the shaft 156 within the cylindrical region 124 of the first elongated member 120. FIG. 5D illustrates the arm articulation regions 132, spacer regions 134, and rotational regions 136 of the distal end 130 of the first elongated member 120. The rotational regions 136 provide a groove that extends circumferentially around the entire distal end 130 which enables the locked configuration of the distal ends 130, 160, described in further detail below with reference to FIG. 11. The distal end 160 of the second elongated member 140 is illustrated as extending within the center of the distal end 130 of the first elongated member 120. In addition, the tension members 210 are routed radially external to the distal end 130 of the first elongated member 130. FIG. 5E illustrates the channels 162 and stops 164 of the distal end 160 of the second elongated member 140. Likewise, the tension members 210 are routed radially external to the distal end 160 of the second elongated member 140. FIG. 5F illustrates the orientations of the medial segments 184 of the arm members 180 with respect to the tension members 210.

Reference is next made to FIG. 6, which illustrates a detailed perspective view of the distal segment 190 of a single arm member of the hernia repair system 100. The intercoupling between the medial segment 184 and the distal segment 190 is representative of the intercoupling scheme utilized between the other segments. The distal segment 190 includes segment portion 189 with a female region 187 disposed opposite to the distal most end. A corresponding male portion 188 of the medial segment 184 is positioned within the female region 187 of the segment portion 189 and coupled via a pin 186. The pin 186 enables a rotational articulation between the medial segments 184 and segment portion 189 of the distal segment 190. In addition, the shape of the male and female regions 188, 187 restrict the relative rotational articulation. The female region 187 includes a lengthwise recess only exposed on one lengthwise side (illustrated upward) of the segment portion 187. Therefore, the opposite side of the segment portion 189 is covered, restricting the male region 188 from rotationally articulating in one direction beyond a substantially lengthwise parallel configuration. The male region 188 therefore is only able to rotate within a substantially ninety degrees of freedom with respect to the female region 187. The distal segment 190 further includes a needle retaining member 192 moveably coupled to the segment portion 189 via a pin 186 on an opposite lengthwise side of the medial segment 184. The needle retaining member 192 includes two recesses 196, 197 for releasably housing a first and second needle 198, 199 respectively. In addition, the tension members 210 are rigidly coupled to the needle retaining member 192 via a tab 194. The moveable coupling of the needle retaining member 192 enables a substantially ninety degree rotational freedom of the needle retaining member 192 with respect to the segment portion 189. As will be described in further detail below, the articulation position of the needle retaining member 192 with respect to the segment portion 189 is determined in part by the tension on the tension member 210. The needles 198, 199 are coupled to a first and second suture 201, 202 to facilitate coupling the mesh (not shown) over the distal side of a herniated region.

Reference is next made to FIG. 7, which illustrates a profile view of the proximal ends 122, 142 of the first and second elongated member 120, 140 of the hernia repair system 100 in an assembled configuration. The operation of the system 100 is controlled by the relative positioning of the proximal ends 122, 142 to enable a user to externally manipulate the distal ends 130, 160 without unnecessarily invasively exposing the surgical region. The proximal end 142 is coupled to the square region 146 of the second elongated member 140 via the locking pin 144. The shape of the square region 146 corresponds to proximal opening to the internal region 126 on the proximal end 122 of the first elongated member 120. The proximal end 122 is coupled to the cylindrical region 124.

Figure 8:
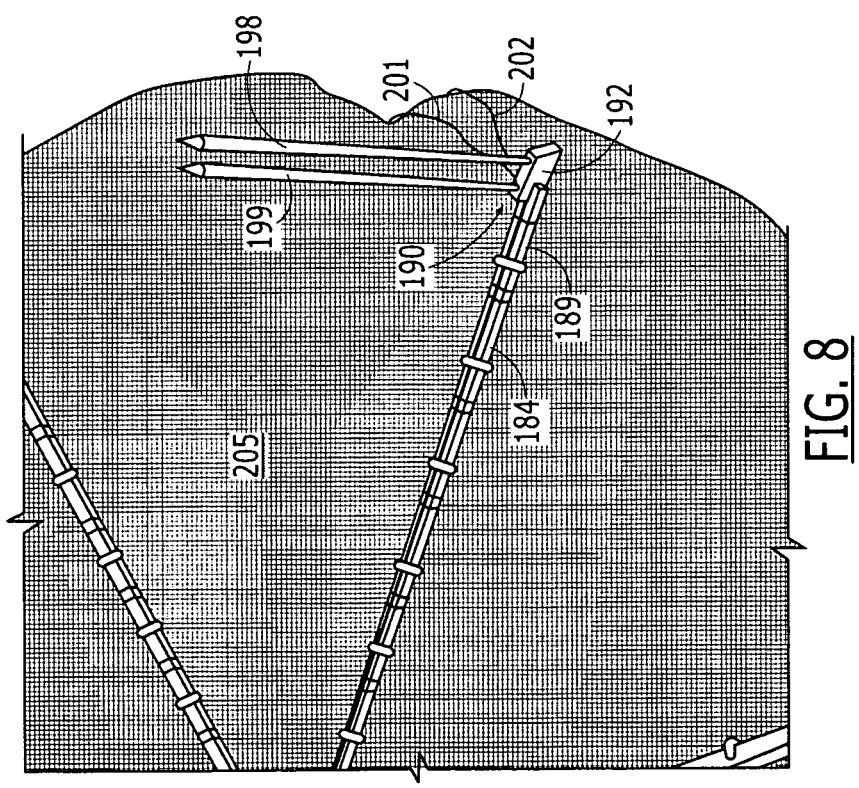
FIG. 8 illustrates a detailed perspective view of the mesh coupled to the distal side of the arm members of the hernia repair system illustrated in FIG. 1.

Reference is next made to FIG. 8, which illustrates a detailed perspective view of the mesh 205 coupled to the distal side of the arm members 180 in a radially extended configuration of the hernia repair system 100. The mesh 205 is a flexible material designed to cover the hernia defect in a two dimensional fashion. Various well known mesh or implant type materials may be utilized in accordance with embodiments of the present invention. The mesh 205 includes two sutures 201, 202 which extend across and around the distal side (not shown) of the mesh 205 to facilitate suturing. The sutures 201, 202 may also be any type of convention sutures in accordance with embodiments of the present invention. The sutures 201, 202 are coupled to the lengthwise end of the needles 198, 199 disposed within the recesses of the needle retaining member 192. The needle retaining member 192 is oriented with respect to the segment portion 189 and the arm members 180 such that the needles 198, 199 are oriented perpendicular to the mesh 205 to enable routing the needles 198, 199 through the edges of the hernia defect. As will be discussed in more detail below, the specific positions of the needle retaining member 192 and overall lengthwise configuration of the arm members 180 corresponds to the tension of the tension members 210 and the relative positioning of the proximal ends 122, 142 of the first and second elongated member 120, 140.

Figure 9A:
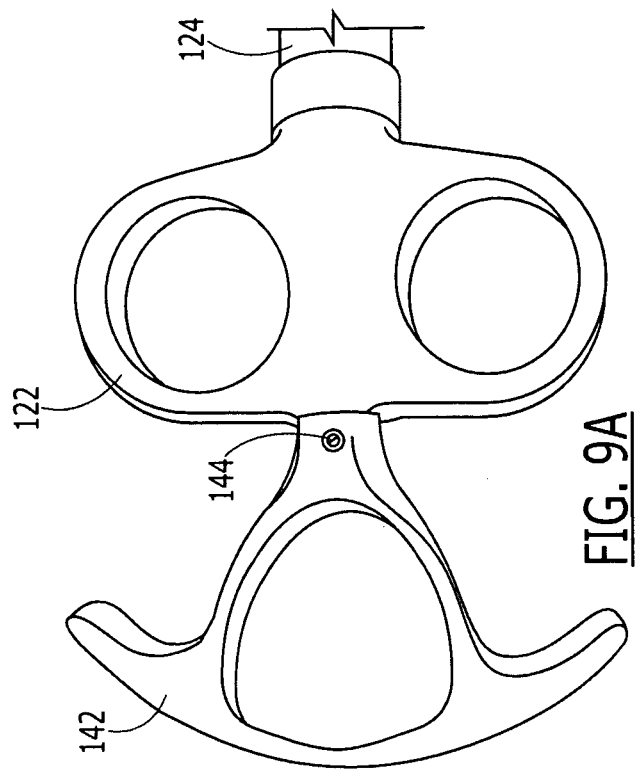

Reference is next made to FIGS. 9A-9B, which illustrate perspective views of the proximal ends 122, 142 of the first and second elongated member 120, 140 corresponding to two different operational states of the hernia repair system 100. FIG. 9A illustrates an unlocked in which the proximal ends 122, 142 are rotationally aligned with one another. The unlocked configuration corresponds to the distal end 160 of the second elongated member 140 being rotationally aligned with the distal end 130 of the first elongated member 120 to enable distal articulation of the arm members 180, as illustrated in FIGS. 3 and 4. In addition, the proximal ends 122, 142 are translationally disposed adjacent to one another in the unlocked or distal freedom configuration such that the distal-most region of the second elongated member 140 proximal end 142 is adjacent to the proximal-most region of the first elongated member 120 proximal end 122. As described above, the unlocked configuration corresponds to a particular rotational alignment of the distal ends 130, 160 to enable distal articulation of the arm members 180. The particular configuration of the proximal ends 122, 142 may also be referred to as a distal freedom configuration because the arm members 180 are enabled to lengthwise articulate freely between the radial extended and distal lengthwise extended configurations. Operationally, the system 100 is initially inserted through a trocar with the proximal ends 122, 142 in the unlocked configuration (FIG. 9A) to enable a particular unlocked rotational alignment of the distal ends 160, 130 (FIG. 10) and the arm members 180 to be positioned within a distal extended configuration (FIG. 12) that is capable of being contained within the diameter of the internal channel of the trocar. As will be described further below in reference to FIG. 10, the tension members 210 are sized and positioned so as to have little or no tension in the unlocked configuration of the proximal ends 122, 142. Therefore, the tension members 210 do not exert any substantial tension forces affecting the articulation position of the arm members 180 in the unlocked configuration.

FIG. 9B illustrates the locked configuration in which the proximal ends 122, 142 are translationally separated and rotated with respect to one another. The second elongated member 140 proximal end 142 is retracted or translated proximally away from the first elongated member 120 proximal end 122, causing the flat region 146 to extend a particular distance through the proximal opening to the internal channel 126 such that the notch 148 is translationally aligned with the proximal opening. The notch 148 of the second elongated member 140 enables the second elongated member 140 to be rotated with respect to the first elongated member 120 within the flat shaped proximal opening of the first elongated member 120. The rotation of the proximal end 142 of the second elongated member 140 corresponds to a rotation of the distal end 160. The direction and degree of rotation between the proximal ends 142, 122 may be determined by the shape of the notch 148. The notch 148 may be specifically shaped to limit the rotation of the second elongated member 140 to ensure accurate rotational positioning of the distal end 160 of the second elongated member 140 with respect to the distal end 130 of the first elongated member 120. The illustrated extended and rotational position of the proximal ends 142, 122 corresponds to both tensioning the tension members 210 and rotating the distal end 160 of the second elongated member 140 with respect to the first elongated member 120. Operationally, the proximal ends 122, 142 are subsequently manipulated by a user into the locked configuration (FIG. 9B) to enable a particular locked rotational alignment of the distal ends 160, 130 (FIG. 11) that locks the arm members 180 into a radial extended configuration (FIG. 13). The radial extended configuration of the system 100 is capable of attaching and suturing the mesh over the herniated region. Since the tension members 210 are rigidly coupled to both the first and second elongated members 120, 140, the relative extension or translation causes a tension force in the tension members 210 which will be described further below with reference to FIGS. 11 and 13.

Reference is next made to FIG. 10, which illustrates a detailed perspective view of the distal ends 130, 160 of the first and second elongated members 120, 140 in an unlocked configuration of the hernia repair system 100. The unlocked configuration of the distal ends 130, 160 corresponds to a rotational alignment of the channels 162 with the arm articulation regions 132. Likewise, the stops 162 are rotationally aligned with the spacer regions 134. Because of the adjacent positioning of the proximal ends 122, 142 (FIG. 9A), the tension members 210 are not tensioned and therefore do not exert any substantial forces upon the arm members 180 in this configuration. The positioning of the distal ends 160, 130 enables the proximal segments 182 of the arm members 180 to articulate within an approximate ninety degree freedom between a perpendicular (shown) position and a substantially parallel lengthwise position. The proximal segments 182, articulate lengthwise within the articulation regions 132 and channels 162 of the distal ends 130, 160 respectively.

Figure 11:
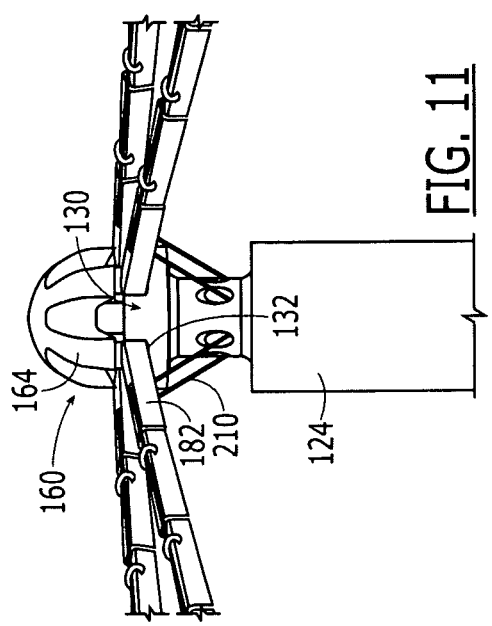
FIG. 11 illustrates a detailed perspective view of the distal ends of the first and second elongated members in a locked configuration of the hernia repair system illustrated in FIG. 1.

Reference is next made to FIG. 11, which illustrates a detailed perspective view of the distal ends 130, 160 of the first and second elongated members 120, 140 in a locked configuration of the hernia repair system 100. The second elongated member 140 distal end 160 is rotated with respect to the first elongated member 130 distal end 130 such that the stops 164 are rotationally aligned with the arm members 180 and the arm articulation regions 132. The relative rotational positioning of the distal ends 130, 160 locks or substantially restricts the articulation freedom of the proximal segment 182 of the arm members 180 into the illustrated radial or perpendicular configuration with respect to the first elongated member 120. Because of the corresponding separation of the proximal ends 122, 142 (FIG. 9B), the tension members 210 become taut and exert a radially-oriented tension force upon the arm members 180 and effectively restrict the medial and distal segments 184, 190 into the radially extended configuration FIG. 13).

Reference is next made to FIG. 12, which illustrates a detailed perspective view of the arm members 180, mesh 205, and the distal ends 160, 130 of the first and second elongated members 120, 140 in a distal lengthwise extended configuration of the arm members 180 of the hernia repair system 100. The lengthwise extended configuration of the arm members 180 corresponds to the unlocked configurations of the distal and proximal ends 130, 160, 122, 142 of the first and second elongated members 120, 140. The arm members 180 extend substantially lengthwise away from the distal ends 130, 160 in a distal direction. The mesh 205 is disposed between the arm members 180. The arm members 180 are substantially lengthwise aligned including lengthwise alignment of the proximal, medial, and distal segments 182, 184, 190. However, the unlocked configuration of the distal and proximal ends 130, 160, 122, 142 of the first and second elongated members 120, 140 corresponds to articulation freedom of the arm members 180, and therefore they are not locked into the lengthwise extended configuration. Likewise, the tension members 210 are not taut and do not exert any form of tension force upon the arm members 180 into the lengthwise extended configuration. The male-female pin type coupling described in detail with reference to FIG. 6, between the segments 182, 184, 190 prevents the inward articulation of the arm members 180 beyond the lengthwise extended configuration. The pin retaining members 192 are illustrated in a radial oriented configuration but are capable of articulating such that the needles (not shown) are proximally oriented and lengthwise folded against the corresponding arm members 180. Therefore, as the system 100 is operationally initially inserted into a trocar, the needles (not shown) extending from the needle retaining members 192 will be forced to articulate proximally to enable lengthwise alignment and system containment within the trocar channel.

Reference is next made to FIG. 13, which illustrates a detailed perspective view of the arm members 180, mesh 205, and the distal ends 130, 160 of the first and second elongated members 120, 140 in a radially extended configuration of the arm members 180 of the hernia repair system 100. The radially extended configuration of the arm members 180 corresponds to the locked configurations of the distal and proximal ends 130, 160, 122, 142 of the first and second elongated members 120, 140. The arm members 180 are radially extended substantially perpendicular to the first and second elongated members 120, 140. The corresponding locked configuration of the proximal ends 122, 142 causes the tension members 210 to be taut, thereby exerting a tension force across the arm members 180. Because of the routing configuration of the tension members 210, this causes the arm members 180 to be radially extended with respect to the distal ends 130, 160. The mesh 205 is positioned on the distal side of the arm members 180. The tension members 210 are directly coupled to the needle retaining members 192, and therefore the tension force also causes the needle retaining members 192 to orient the needles proximally substantially perpendicular to the arm members 180. In operation, the arm members 180 are extended into the radial extended configuration upon being disposed distal of the herniated region such that the mesh 205 may be appropriately positioned on the distal side of the entire herniated region. The orientation of the needles 201, 202 enables a user to then retract the entire system and cause the needles to pierce the fascial edges around the herniated region to enable external suturing of the mesh 205 over the herniated region.

Figure 14:
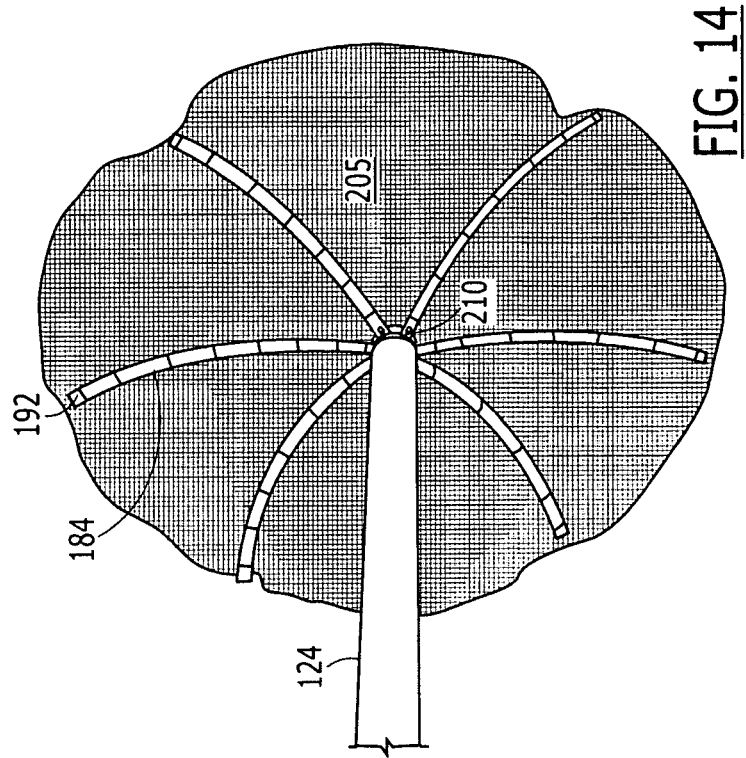
FIG. 14 illustrates a detailed perspective view of the arm members and the distal ends of the first and second elongated members in a partially retracted configuration of the hernia repair system illustrated in FIG. 1.

Reference is next made to FIG. 14, which illustrates a detailed perspective view of the arm members 180 and the distal ends 130, 160 of the first and second elongated members 120, 140 in a partially retracted configuration of the hernia repair system 100. The illustrated partially retracted configuration corresponds to the unlocked configurations of the distal and proximal ends 130, 160, 122, 142 of the first and second elongated members 120, 140. The arm members 180 are illustrated in a partially articulated configuration representing the process through which the arm members 180 are retracted from between the herniated region and the mesh 205. The articulation freedom of the arm members in the unlocked configurations enables the individual segments 182, 184, 190 of each arm member to articulate proximally lengthwise to correspond to the extraction position. Therefore, the arm members 180 may be retracted from a narrow region contained between the mesh 205 and the hernia.

In operation, systems in accordance with the present invention may be utilized to insert and attach a mesh over the distal side of a herniated region via the herniated opening itself. A trocar is positioned through the herniated opening so as to provide a proximal to distal channel extending externally to internally. Initially, the system 100 is in the unlocked configurations (FIG. 9A and 10) of the distal and proximal ends 130, 160, 122, 142 of the first and second elongated members 120, 140, including a substantially distal extended configuration of the arm members 180 (FIG. 13). The system 100 is initially translationally distally inserted by a user through the internal channel of a trocar until the arm members 180 and distal ends 130, 160 are distal to the hernia. An optional telescoping sleeve may be utilized to contain the arm members 180 within the distal extended configuration (FIG. 12) during insertion. The optional sleeve may then be automatically or manually telescopically retracted proximally from the arm members 180 and distal ends 130, 160 once the arm members 180 and distal ends 130, 160 are distally disposed with respect to the hernia. The user may then proximally retract and subsequently rotate the second elongated member 140 proximal end 142 from the first elongated member 120 proximal end 122 causing engagement of the locked configurations (FIGS. 9B and 11) and substantial locking of the arm members 180 into the radial extended configuration (FIG. 14). The user may then proximally translate the entire system 100 so as to extend the needles 198, 199 through the abdominal wall around the herniated region and position the mesh 205 over the distal side of the herniated region. The needles may then be externally interwoven to suture the mesh 205. Various needle release systems may be utilized to release the needles from the needle retaining members. The user may then oppositely rotate and subsequently distally translate the second elongated member 140 proximal end 142 with respect to the first elongated member 120 proximal end 122, disengaging the locked configurations into the unlocked configurations (FIG. 9A and 10) of the distal and proximal ends 130, 160, 122, 142 of the first and second elongated members 120, 140. The reverse rotation is oriented opposite to the rotation used to engage the locked configurations. The unlocked configurations enable the segments 182, 184, 190 of the arm members 180 to independently articulate within a lengthwise proximal orientation. The user then proximally retracts the system 100 from between the mesh 205 and the herniated region. As the segments 182, 184, 190 translate into the internal channel of the trocar, they are forced to individually articulate by varying degrees to enable the retraction. The arm members 180 are thereby proximally lengthwise articulated from the radial extended configuration back to the lengthwise distal extended configuration over the course of the retraction process.

Various other embodiments have been contemplated, including combinations in whole or in part of the embodiments described above. Various additional components and or materials may be used in conjunction with embodiments of the present invention.

What is claimed is:

1. A hernia repair system comprising:
    a first elongated member having a distal end, a proximal end, and an internal channel extending therebetween, wherein the distal end includes a distal opening to the internal channel and the proximal end includes a proximal opening to the internal channel;
    a second elongated member extending through the internal channel of the first elongated member, wherein the second elongated member includes a locking member disposed on a distal end;
    a plurality of arm members moveably coupled to the distal end of the first elongated member, wherein the arm members each comprise a plurality of moveably intercoupled segments, wherein the moveable coupling of the arm members to the first elongated member is restricted to limit the articulation of the arm members between a lengthwise extended distal configuration and a radial extended configuration, and wherein the arm members further include a distal segment disposed on a lengthwise end of each arm member opposite the moveable coupling with the first elongated member;
    a plurality of tension members rigidly coupled to and extending between the distal segment of each of the plurality of arm members and the second elongated member, wherein the tension of the plurality of tension members corresponds to the configuration of the plurality of arm members, and wherein the plurality of tension members extend substantially adjacent to the plurality of segments and through the internal channel of the first elongated member;
    wherein the radial extended configuration includes a proximal translational displacement of the second elongated member with respect to the first elongated member, a tension in the plurality of tension members, and a radial extended position of the plurality of arm members substantially perpendicular to the first elongated member; and
    a mesh releasably coupled to a distal side of the plurality of arm members in the radial extended configuration.

2. The hernia repair system of claim 1, wherein the moveable intercoupling between the segments is restricted to within a ninety degree lengthwise radial articulation.

3. The hernia repair system of claim 1, wherein the moveably intercoupled segments comprise:
    a rectangular body with a first and second end;
    a hooded female region disposed on the first end; and
    a male region disposed on the second end, wherein the male region is configured to be disposed within the hooded female region of an adjacent segment and wherein a pin is perpendicularly extended through the male segment and the adjacent hooded female segment creating the moveable intercoupling therebetween.

4. The hernia repair system of claim 3, wherein the moveable intercoupling between the male and female regions of adjacent segments enables a lengthwise articulation about the pin, and wherein a hooded portion of the female region restricts the lengthwise articulation angle between the segments to substantially ninety degrees of lengthwise articulation.

5. The hernia repair system of claim 1, wherein the individual moveable coupling of the arm members to the first elongated member is restricted to within a ninety degree lengthwise radial articulation.

6. The hernia repair system of claim 1, wherein the distal segment of each arm member includes a needle retaining member and at least one needle, and wherein the needle is releasably coupled to the needle retaining member and the mesh.

7. The hernia repair system of claim 1, wherein the lengthwise extended distal configuration includes the plurality of arm members lengthwise distally extended substantially parallel with the first elongated member.

8. The hernia repair system of claim 1, wherein the distal end of the second elongated member includes a locking member comprising a plurality of radial channels and radial stops, wherein the radial extended configuration includes alignment of the radial stops with the plurality of arm members thereby restricting the plurality of arm members from distally lengthwise extending beyond the substantially perpendicular orientation with respect to the first elongated member.

9. The hernia repair system of claim 1, wherein the distal segments of each arm member include a needle retaining member, and wherein the needle retaining members releasably support a plurality of suture needles intercoupled to one another and the mesh, and wherein the coupling between the needle retaining members and the arm members is configured such that the suture needles are proximally oriented parallel to the first elongated member in the radial extended configuration and the distal lengthwise configuration.

10. The hernia repair system of claim 1, wherein the number of segments included in each arm member and the orientation of the moveable intercoupling between the segments corresponds to the lengthwise articulation freedom of each arm member.

11. The hernia repair system of claim 1, wherein proximal end of the first elongated member includes a finger handle, and wherein the proximal end of the second elongated member includes a thumb handle.

12. The hernia repair system of claim 1, wherein the radial extended configuration further includes a locked configuration and an unlocked configuration, wherein the locked configuration corresponds to a rotational position of the distal end of the second elongated member that restricts the plurality of arm members from distally lengthwise extending beyond the substantially perpendicular orientation with respect to the first elongated member.

13. The hernia repair system of claim 12, wherein each arm member includes a proximal segment at which the arm member is moveably coupled to the first elongated member, wherein the rotational position of the distal end of the second elongated member in the locked configuration substantially restricts all movement freedom of the proximal segment.

14. The hernia repair system of claim 1, wherein the system is particularly configured for at least one of a ventral, incisional, and umbilical hernia repair.

15. The hernia repair system of claim 1, wherein the lengthwise extended distal configuration further includes a deployment sub-configuration and a retraction sub-configuration corresponding to the deployment and retraction phases of the corresponding operative procedure, and wherein the deployment sub-configuration includes the mesh disposed within the three dimensional region between the arm members.

16. The hernia repair system of claim 1, wherein the mesh is releasably coupled to a needle retaining member of the plurality of arm members.

17. A self-contained ventral hernia repair system comprising:
a first elongated member having a distal end, a proximal end, and an internal channel extending therebetween, wherein the distal end includes a distal opening to the internal channel and the proximal end includes a proximal opening to the internal channel;
a second elongated member extending through the internal channel of the first elongated member, wherein the second elongated member includes a locking member disposed on a distal end;
a plurality of arm members moveably coupled to the distal end of the first elongated member, wherein the arm members each comprise a plurality of moveably intercoupled segments, wherein the moveable intercoupling between the segments is restricted to within a ninety degree lengthwise radial articulation, and wherein the moveable coupling of the arm members to the first elongated member and the moveable intercoupling between the segments is restricted to articulate between a lengthwise extended distal configuration and a radial extended configuration, wherein the arm members further include a needle retaining member moveably coupled to the distal most segment of each arm member;
a plurality of tension members rigidly coupled to and extending between the needle retaining member of each of the plurality of arm members and the second elongated member, wherein the tension of the plurality of tension members corresponds to the configuration of the plurality of arm members, and wherein the plurality of tension members extend substantially adjacent to the plurality of segments and through the internal channel of the first elongated member external to the second elongated member;
wherein the radial extended configuration includes a proximal translational displacement of the second elongated member with respect to the first elongated member, a tension in the plurality of tension members, and a radial extended position of the plurality of arm members substantially perpendicular to the first elongated member;
wherein the lengthwise extended distal configuration includes the plurality of arm members lengthwise extended such that the needle retaining member is disposed distal of the distal end of the first elongated member; and
a mesh releasably coupled to a distal side of the plurality of arm members in the radial extended configuration.

18. A method for distally coupling a mesh over a ventral hernia in the abdominal wall and subsequently removing the remainder of the hernia repair system, comprising the acts of:
providing a trocar extending through a hernia in the abdominal wall of a patient including an internal channel extending between a proximal end of the trocar disposed external to the patient and a distal end of the trocar disposed distal of the hernia;
providing a hernia repair system comprising:
a first elongated member having a distal end, a proximal end, and an internal channel extending therebetween, wherein the distal end includes a distal opening to the internal channel and the proximal end includes a proximal opening to the internal channel;
a second elongated member extending through the internal channel of the first elongated member, wherein the second elongated member includes a locking member disposed on a distal end;
a plurality of arm members moveably coupled to the distal end of the first elongated member, wherein the arm members each comprise a plurality of moveably intercoupled segments, and wherein the arm members further include a distal segment disposed on a lengthwise end of each arm member opposite the moveable coupling with the first elongated member;

a plurality of tension members rigidly coupled to and extending between the distal segment of each arm member and the second elongated member;

a mesh releasably coupled to a distal side of the plurality of arm members in the radial extended configuration;

inserting the hernia repair system through the internal channel of the trocar such that the plurality of arm members are distal of the trocar;

radially extending the arm members substantially perpendicular to the first elongated member;

coupling the mesh over a distal opening to the hernia and releasing the mesh from the plurality of arm members; and retracting the arm members from between the mesh and hernia into the internal channel of the trocar; and retracting the hernia repair system from the internal channel of the trocar.

19. The method of claim 18, wherein the act of radially extending the arm members substantially perpendicular to the first elongated member comprises:

proximally translating the second elongated member from the first elongated member thereby inducing a tension on the tension members;

tensioning the moveably intercoupled segments of each arm member substantially parallel;

tensioning each arm member into a radial extended configuration in which the lengthwise orientation of each arm member is substantially perpendicular with respect to the first elongated member;

rotating the second elongated member with respect to the first elongated member locking the arm members in the radial extended configuration.

20. The method of claim 18, wherein the act of coupling the mesh over a distal opening to the hernia and releasing the mesh from the plurality of arm members further comprises:

proximally partially retracting the first and second elongated member;

extending a plurality of interwoven needles disposed on the distal segment of each arm member through the abdominal wall.

21. The method of claim 18, wherein the act of retracting the arm members from between the mesh and hernia into the internal channel of the trocar includes individually articulating the moveably intercoupled segments from one another enabling corresponding lengthwise proximal oriented articulation of each of the arm members.

22. The method of claim 21, wherein the act of individually articulating the moveably intercoupled segments includes progressively articulating the segments with respect to the proximity to the hernia.

* * * * *